United States Patent [19]

Yoshizawa et al.

[11] 4,237,232

[45] Dec. 2, 1980

[54] METHOD OF PURIFYING DISTILLERS SOLUBLES AND USE OF THE PURIFIED MATTER

[75] Inventors: Kiyoshi Yoshizawa, Tokyo; Kikuo Nojiro, Machida; Masamitsu Itoh, Hatoyama; Hiroshi Kiuchi, Sayama; Kazuo Horii, Otani-Omiya, all of Japan

[73] Assignees: National Tax Administration Agency; Kibun Company Limited, both of Tokyo, Japan

[21] Appl. No.: 902,225

[22] Filed: May 2, 1978

Related U.S. Application Data

[62] Division of Ser. No. 762,680, Jan. 26, 1977.

[30] Foreign Application Priority Data

| May 6, 1976 | [JP] | Japan | 51/50746 |
| May 6, 1976 | [JP] | Japan | 51/50747 |
| May 6, 1976 | [JP] | Japan | 51/50748 |
| Jun. 17, 1976 | [JP] | Japan | 51/70428 |
| Sep. 2, 1976 | [JP] | Japan | 51/104235 |

[51] Int. Cl.$^3$ .......................... C12N 1/00; C12N 1/20; C12N 1/14; C12N 1/16
[52] U.S. Cl. .................................. 435/243; 435/253; 435/254; 435/255; 435/256; 260/236.5
[58] Field of Search ............... 195/100, 101, 102, 103; 426/624, 615, 478, 490, 495; 260/236.5; 435/243, 253, 254, 255, 256

[56] References Cited

U.S. PATENT DOCUMENTS

| 2,263,608 | 11/1941 | Brown | 426/624 |
| 2,302,393 | 11/1942 | Schopmeyer | 426/495 |

OTHER PUBLICATIONS

Beeson et al., "In vitro Studies on the Effect of Screened and Centrifuged Processed Corn Distillers Solubles on Cellulose Digestion and Microbial Synthesis of Protein", *Distill. Feed Res. Counc. Conf.*, Proc., vol. 31, (1976), pp. 8–15.

Boruff, "Recovery of Fermentation Residues as Feeds", *Industrial and Engineering Chem.*, vol. 39 (1947), pp. 602–607.

Michaels, "New Separation Technique for the CPI", *Chem. Eng. Prog.*, vol. 84, No. 12, (1968), pp. 31–43.

*Primary Examiner*—Thomas G. Wiseman
*Attorney, Agent, or Firm*—Browdy and Neimark

[57] ABSTRACT

Distillers solubles are purified by a centrifugal separation to a degree above 50,000, which is the product of g × minute, or a filtration with addition of a filter aid. The clarified matter is purified by a molecular sieve treatment, ultrafiltration, reverse osmosis or an organic solvent precipitation. The clarified matter or purified matter thus obtained is pulverized by spray drying, lyophilic drying or air drying.

Said clarified matter, purified matter or pulverized matter is added to a fermentation medium or a feed as an available component.

5 Claims, No Drawings

METHOD OF PURIFYING DISTILLERS SOLUBLES AND USE OF THE PURIFIED MATTER

This is a division of application Ser. No. 762,680 filed Jan. 26, 1977.

FIELD OF INVENTION

The present invention relates to a method of purifying distillers solubles.

An object of the present invention is to remove contaminants from distillers solubles, and to provide a fermentation medium and an available component of feed thus utilizing it. Although the available component obtained and utilized by the present invention is one which has been unknown and not been identified, this component is referred to herein as distillers solubles unknown growth factor. Hereinafter the available component of the present invention is abbreviated simply as DSUGF.

BACKGROUND OF INVENTION

In general, the distillers solubles are generally deformed as, for example, distillation residues soluble or suspended in water and from which the rough parts of the particles have been removed, such residues being from stillage (residue of distillation) of whisky and so on, and they may be dried into dried solubles or concentrated or made into semisolid state and added to feed, thus having been broadly utilized.

Also, these distillers solubles have been known for their effects as a growth source of Actinomyces and other various microorganisms or as a growth promoting factor and thereby have been broadly used.

However, even such useful distillers solubles have large drawbacks in use. For example, in the case where the distillers solubles are used as growth source of microorganisms, as they are or in concentrated state, many suspended contaminants and lipid materials may contaminate the microorganisms cells or products; but the removing thereof is very difficult, so that they can not be possibly used for propagation of cells which are adapted for food, such as bakers yeast, starter and so on as they are. Also such distillers solubles have never been utilized for products which are difficult to purify. Moreover, the distillers solubles concentrated and formed into solid state have poor solubility, and in use they are inconvenient, so that they have been difficult to use as a general source of culture.

Heretofore, the distillers solubles sold in market generally are those produced by removing large solids from stillage of whisky or the like, and concentrated, and it has been believed that the distillers solubles themselves constitute an available component as a whole.

SUMMARY OF INVENTION

Studies have now been conducted to modify the properties of such distillers solubles to allow the use thereof, for example, as a substitute for yeast extract, and as a result it was found unexpectedly that the distillers solubles can be rapidly clarified by a centrifugal treatment or a filtration treatment, and the resultant clarified liquid has a large amount of DSUGF and if said liquid is subjected to further purifying process, its available component can be more concentrated.

The present invention relates to fermentation medium and feed which are produced by subjecting distillers solubles or their concentrate to a centrifugal treatment or a filtration treatment, and, if necessary, the resultant supernatant to a further purifying treatment, and allowing them to contain the resultant clarified liquid or its treated matter thus obtained therein as DSUGF.

The distillers solubles used in the present invention may be any one of stillages such as whisky stillage, grain alcohol stillage and so on, and these unconcentrated liquids, partly concentrated concentrates and a marketed matter concentrated to 1/5–1/10 ratio by volume are adapted to the present invention as they are.

According to the present invention, a centrifugal treatment or a filtration treatment is adopted to obtain clarified filtrate.

DETAILED DESCRIPTION OF EMBODIMENTS

In the centrifugal treatment, defatting is not caused, so that if defatting is carried out previously, the clarified liquid can be obtained directly by the centrifugal treatment. To carry out such a previous defatting, these distillers solubles or their relevant matter is contacted with an organic solvent such as ether etc. and the portions extracted and removed therefrom. This defatting process is not an indispensable one before the centrifugal treatment, but an optional one, and if it is not carried out before the centrifugal treatment, it is sufficiently done after the centrifugal treatment by solvent extraction and filtration etc.

The centrifugal separating treatment of distillers solubles herein is carried out to a degree above 50,000, which is the product of g×minute, preferably to a degree above 70,000 (g×minute).

In general, g is represented by the following formula, $$g = S^2 r / 89500$$

s: rpm
r: distance (cm) from rotating shaft to the end of liquid portion.

The degree of centrifugal treatment is represented by a product of g multiplied by minute, that is to say, g×minute.

Herein, using a centrifugal separator of r=9.6 cm, unconcentrated liquid of distillers solubles was defatted by ether, and subjected to centrifugal treatments of various g, and the resultant clarified liquids were measured of their turbidity by means of a wave length of 660 nm, and thereby the results shown in the following Table 1 were obtained.

TABLE 1

| g | Time (minute) | g × minute | Degree of transmission(%) |
|---|---|---|---|
| 965 | 10 | 9650 | 0.300 |
| 1716 | 10 | 17160 | 0.265 |
| 2681 | 10 | 26810 | 0.070 |
| 3861 | 10 | 38610 | 0.060 |
| 5255 | 10 | 52550 | 0.050 |
| 6864 | 10 | 68640 | 0 |
| Unconcentrated liquid of distillers solubles | | | 56 |
| Defatted liquid of unconcentrated liquid by ether | | | 13 |

Also, using a constant g (10733 g), the same ether defatted unconcentrated liquid of distillers solubles was subjected to centrifugal treatments with various times, and the resultant supernatants were measured of their turbidity by means of a wave length of 660 nm, and thereby the results shown in the following Table 2 were obtained.

TABLE 2

| g | Time (minute) | g × minute | Degree of transmission(%) |
|---|---|---|---|
| 10733 | 3 | 32199 | 0.070 |
| 10733 | 4 | 42932 | 0.060 |
| 10733 | 5 | 53665 | 0.040 |
| 10733 | 6 | 64398 | 0.020 |
| 10733 | 7 | 75131 | 0 |
| Unconcentrated liquid of distillers solubles | | | 56 |
| Defatted liquid of unconcentrated liquid by ether | | | 13 |

From these results, it is obvious that the distillers solubles can be fairly clarified by centrifugation to a degree above 50,000 (g×minute) and completely clarified by centrifugation to a degree 70,000 (g×minute).

The obtained light fulvous transparent liquid has lipid material suspended therein in the case where defatting has not been carried out before the centrifugal separation treatment, and therefore if it is subjected to a filtration by means of a thick filter paper, for example, Whatman filter paper No. 32, the fat can be separated easily.

Also, according to the present invention, in the case the distillers solubles are filter treated, this is carried out under addition of a filter aid to the distillers solubles. As filter aids, celite, talc, paper pulp, saw dust, short fibers and so on are used effectively.

To the distillers solubles or their concentrate, a filter aid is added in an amount of 1–10%, and the mixture is sufficiently stirred and filtered.

The filtration may be of the continuous type or the batch type, however, filtration under pressure or vacuum is preferable in efficiency, and therefore continuous type drum filter machines etc. are most preferable as means of industrial filtering.

The obtained matter by the centrifugal treatment or filtration treatment is light fulvous transparent liquid which is quite different from the distillers solubles of dark brown mud like property which has been heretofore known, and is thought a distinct one therefrom.

The light fulvous transparent liquid contains almost all of DSUGF and therefore is very effective as various kinds of microogranisms fermentation medium and feed. Since this transparent liquid is free of suspended contaminant, it can be broadly used for culture of edible fungi, production of starter and bakers yeast and so on, and therefore becomes very useful.

Thus obtained transparent supernatant is effective as it is, but from the view point of contained components, in a low molecular range and in a high molecular range a fairly large amount of matter is contained in said supernatant, and it is thought that a true available component or a group of available components exist therein. According to the present invention, it is possible that this supernatant is subjected to a treatment such as ultrafiltration etc., if necessary, thereby separating a liquid containing low molecular matter group and a high molecular material group and thus notably concentrating DSUGF.

In order to obtain liquids containing low molecular matters and high molecular matters, any means can be adopted, such as use of molecular sieve, membrane filter and so on, and it is industrially effective to use an ultrafiltration using a cheap membrane filter. For the ultrafiltration, various kinds of membrane filters can be used, and for example, membrane filters made by Amicon Co., XM-100, UM-10, UM-2, UM-05 etc. can be combined to obtain a liquid containing matters of various molecular weights. In this case, if a liquid part passing through UM-05 is separated, low molecular matters containing liquid can be obtained, and if a liquid part not passing through UM-05 is separated, high molecular matters group containing liquid can be obtained, and said high molecular matters containing liquid can be further graduated into respective molecular weight matters group containing liquids of about $10^3$–$10^4$, $10^4$–$10^5$ and above $10^5$ of molecular weight respectively by using UM-2, UM-10 and XM-100 etc.

The unconcentrated liquid of distillers solubles was subjected to a centrifugal treatment after defatting process, and the obtained clarified liquid was passed through each membrane filter, and the resultant liquid part and its five times concentrate were measured to determine the amount of nitrogen, and thereby the results shown in Table 3 were obtained.

TABLE 3

Ultrafiltration of defatted liquid of distillers solubles unconcentrated liquid.
(By means of membrane filters, XM-100, UM-10, UM-2, UM-05, made by Amicon Co.)

| Molecular weight | Amount of N | Amount of N of five times concentrate |
|---|---|---|
| Above $10^5$ (XM-100) | 0.082mg/ml | 0.412mg/ml |
| $10^4$–$10^5$ (UM-10) | 0.342 | 1.712 |
| $10^3$–$10^4$ (UM-2) | 0.056 | 0.284 |
| 500–$10^3$ (UM-05) | 0.020 | 0.100 |
| Below 500 | 0.137 | 0.685 |
| Distillers solubles unconcentrated liquid | 0.7 | — |

Wherein amount of N was analyzed by Kjeldahl method, and each fractionated matter was represented by a conversion into distillers solubles unconcentrated liquid.

For example, the resultant liquids containing matters of UM-05 pass and XM-100 pass—UM-10 no pass respectively are very light yellowish transparent solutions containing a large amount of DSUGF, and effective as various kinds of microorganism medium.

Also, the distillers solubles clarified liquid can be fractionated into a high molecular matter group and a low molecular matter group by the reverse osmosis method in very short time. In the case of use of the reverse osmosis method, AS-215, AS-230 and AS-290 etc. (all made by Abcor Co.) are used as RO reverse osmosis membranes, and this method is effective to approximately fractionate DSUGF and purify it. The transparent liquids obtained by these purifying methods are free of contaminants, and therefore these becomes very useful for production of foods and biochemical medicines.

The obtained DSUGF containing liquid does not contain contaminants, so that various kinds of treatments such as concentrating and drying etc. can be carried out thereto. In the case of drying, said liquid is often added with various kinds of salts, sugars and other assistant so as to make suitable at the time of resolution, and mixed therewith and then pulverized by spray drying, lyophilic drying and so on. The obtained condensate and powder are convenient to transport, and at the time of use, can immediately dissolve in water thereby reproducing transparent liquid state, and accordingly these can be added to all media as an available component for propagation of microogranism.

As an effective concentration method for DSUGF, there is a precipitation treatment by means of organic solvents such as ethanol, acetone, methanol etc. The available component of distillers solubles progressively precipitates as the concentration of organic solvent becomes higher, so that the resultant precipitate is filter separated, and the separated precipitate can be used as it is or after being subjected to air drying, and pulverized appropriately. For example, in the case of the use of ethanol to precipitate DSUGF, when it is added up to 50–90% of ethanol final concentrations, almost all of the DSUGF precipitates at respective concentrations, and therefore if these precipitates are individually separated appropriately by filtration or centrifugal separation, DSUGF can be obtained is solid state in notably purified condition. Also, since there are available components such as yeast etc. in the soluble section of above 90%, the liquid part can be distillation removed so as to obtain DSUGF in solid state.

The fermentation medium of the present invention is formed by allowing DSUGF to be contained therein. Forming of the medium is effected by mixing the supernatant together with sugars, various kinds of salts and a very small amount of nutritious source previously, and subjecting the resulant mixture to lyophilic or spray drying, or by mixing the dried supernatant as it is. Forming of the medium can be carried out before the culture. In this case, the supernatant, its condensate, its dried matter etc. are previously provided, and these are mixed with sugars, various kinds of salts, a very small amount of nutrious source etc. thereby forming the fermentation medium.

Addition into the fermentation medium can be carried out in a great amount if this supernatant does not particularly obstruct the culture, and also the substitution for all nitrogen compounds is possible. Relating to amount of addition, it is preferable to add above about 21 mg in 100 ml as amount of nitrogen.

DSUGF of the present invention is effective to the growth of the rumen microorganisms isolated from the rumen, and also stimulates the growth of the rumen microorganisms by giving it to cows, and serves for the growth of cows and the increase of body-weight thereof. It is also very effective for the growth and the increase of body-weight of sheep, pigs, minks, hens, fish etc. besides for cows when adding it to their feed.

Various kinds of feeds according to the present invention are produced by adding the centrifugally treated matter or the filter treated matter of distillers solubles or their concentrate or their further treated matter to general feed component in the state of liquid, concentrate or powder, and mixing them together.

The available component containing feed of the present invention serves notably for promoting of the growth and increasing of body-weight by giving it to cows, sheep, pigs, minks, hens and fish etc.

Next, embodiments of the present invention will be shown in relation to experimental examples, production examples, fermentation examples and feed examples, and the light fulvous transparent liquid obtained in Production example 1 will be expressed as "defatted DS" in some cases.

EXPERIMENTAL EXAMPLE 1

Using the available component of distillers solubles obtained in Production example 1 and the precipitate separated at that time, and using *Lentinus edodes* (IFO 4902) as microorganism, effects to cell propagation of marketed distillers solubles (whisky stillage 1/5 concentrate) and its available component liquid obtained in the method of Production example 1 were examined.

As the basic medium, a medium of the following composition was used:
Glucose—10 g
Yeast extract—2.4 g
Polypeptone—2.4 g
$KH_2PO_4$—1 g
$MgSO_4.7H_2O$—0.5 g
$CaCl_2.2H_2O$—0.5 g
$FeCl_3.6H_2O$—10 mg
$MnCl_2.4H_2O$—7.2 mg
$ZnCl_2$—4.0 mg
$CuSO_4.5H_2O$—1.0 mg
Water—1000 ml
(pH=5.0)

Using this basic medium, the following media were made:

1. Only 100 ml of the basic medium.
2. Such one prepared by adding 1.5 g of the distillers solubles to 100 ml of the basic medium.
3. Such one prepared by adding 1.0 g of the supernatant liquid resulting from a centrifugal treatment to a degree of 70,000 (g×minute) of the distillers solubles (this amount corresponds to 1.5 g of the distillers solubles.) to 100 ml of the basic medium.
4. Such one prepared by adding 0.5 g of the precipitate resulting from a centrifugal treatment to a degree of 70,000 (g×minute) of the distillers soluble (this amount corresponds to 1.5 g of the distillers solubles.) to the basic medium.
5. Such one prepared by removing the yeast extract and polypeptone from the basic medium and adding 1.5 g of the distillers solubles thereto.
6. Such one prepared by removing the yeast extract and polypeptone from the basic medium and adding 1.0 g of the supernatant liquid resulting from a centrifugal treatment to a degree of 70,000 (g×minute) of the distillers solubles (this amount corresponds to 1.5 g of the distillers solubles.) thereto.
7. Such one prepared by removing the yeast extract and polypeptone from the basic medium and adding 0.5 g of the precipitate resulting from a centrifugal treatment to a degree of 70,000 (g×minute) of the distillers solubles (this amount corresponds to 1.5 g of the distillers solubles.) thereto.

100 ml of each of said prepared medium was put in a 500 ml Sakaguchi flask, and *Lentinus edodes (IFO 4902)* was inoculated therein and a shaking culture was carried out at 25° C. and 100 rpm (with 7 cm stroke).

After seven days culturing, the produced cells were collected by a filtration, and dried, and amount of cells in each medium was investigated as the dried matter.

The results are shown in the following Table, and it is obvious from the Table that DSUGF exists in large quantities in the liquid part and very slightly in the precipitate.

TABLE

| Medium number | Amount of dried cells (g/100ml) |
|---|---|
| 1 | 0.36 |
| 2 | 1.98* |
| 3 | 1.35 |
| 4 | 0.72* |
| 5 | 1.05 |
| 6 | 0.94 |

TABLE-continued

| Medium number | Amount of dried cells (g/100ml) |
|---|---|
| 7 | 0.69* |

*In this case, since it is observed that the precipitated solid matters are taken in the fungi pellets and left therein as they are, true weight of the fungi is considered to be fairly less than this value.

EXPERIMENTAL EXAMPLE 2

Using the available component liquid of distillers solubles obtained in Production example 2 and using *Lentinus edodes* IFO 4902 as microorganism, effects to cell propagation of commercial distillers solubles (whisky stillage 1/5 concentrate) and of its available component liquid obtained in the method of Production example 2 were compared with those of yeast extract and of polypeptone.

As the basic medium, a medium of the following composition was used:
Glucose—10 g
Yeast extract—2.4 g
Polypeptone—2.4 g
$KH_2PO_4$—1 g
$MgSO_4.7H_2O$—0.5 g
$CaCl_2.2H_2O$—0.5 g
$FeCl_3.6H_2O$—10 mg
$MnCl_2.4H_2O$—7.2 mg
$ZnCl_2$—4.0 mg
$CuSO_4.5H_2O$—1.0 mg
Water—1000 ml
(pH=5.0)

Using this basic medium, the following media were prepared;
1. Only 100 ml of the basic medium.
2. Such one prepared by adding 1.5 g of the distillers solubles to 100 ml of the basic medium.
3. Such one prepared by adding 1.0 g of the available component liquid resulting from a filter treatment of the distillers solubles (this amount corresponds to 1.5 g of the distillers solubles.) to 100 ml of the basic medium.
4. Such one prepared by adding 1.5 g of the distillers solubles to the basic medium free from yeast extract and polypeptone.
5. Such one prepared by adding 1.0 g of the DSUGF component liquid resulting from a filter treatment of the distillers solubles (this amount corresponds to 1.5 g of the distillers solubles.) to the basic medium free from yeast extract and polypeptone.

100 ml of each of said prepared medium was put in a 500 ml Sakaguchi flask, and a japanese mushroom (*Lentinus edodes* IFO 4902) was inoculated and incubated with shaking at 25° C. and 100 rpm (with 7 cm stroke).

After 7 days of culture, the produced cells were collected by a filtration, and dried, and amount of cells in each medium was investigated as the dry matter.

The results are shown in the following Table, and it is obvious from the Table that the available component of the distillers solubles exists in large quantities in the filter part.

TABLE

| Medium No. | Amount of dried cells (g/100ml) |
|---|---|
| 1 | 0.36 |
| 2 | 0.98* |
| 3 | 1.25 |
| 4 | 0.94* |
| 5 | 0.88 |

*In this case, since it is observed that the precipitated solid matters are taken in the cell pellets and left therein as they are, true weight of the cells is considered to be fairly less than this value.

EXPERIMENTAL EXAMPLE 3

Using the liquid available component of distillers solubles passing through the molecular filter obtained in Production example 3 and each filtrate containing the matter of each molecular weight separated at that time, and using *Lentinus edodes* IFO 4902 (a species of japanese mushroom) as microorganism, and, after regulating an amount of nitrogen at the same level, effects to cell propagation in each medium were examined. The uncondensate of distillers solubles and the basic medium were used as controls.

As the basic medium, a medium of the following composition was used:
Glucose—10 g
Yeast extract—2.4 g
Polypeptone—2.4 g
$KH_2PO_4$—1 g
$MgSO_4.7H_2O$—0.5 g
$CaCl_2.2H_2O$—0.5 g
$FeCl_3.6H_2O$—10 mg
$MnCl_2.4H_2O$—7.2 mg
$ZnCl_2$—4.0 mg
$CuSO_4.5H_2O$—1.0 mg
Water—1000 ml
(pH=5.0)

Using this basic medium, the following media were prepared;
1. Only 100 ml of the basic medium.
2. Such one prepared by removing the yeast extract from the basic medium and add the uncondensate of distillers solubles in same amount of nitrogen as the yeast extract thereto.
3. Such one prepared by removing the yeast extract from the basic medium and adding the liquid passing through UM-05 in the same amount of nitrogen as the yeast extract thereto.
4. Such one prepared by removing the yeast extract from the basic medium and adding the liquid passing through UM-2—no passing through UM-05 in the same amount of nitrogen as the yeast extract thereto.
5. Such one prepared by removing the yeast extract from the basic medium and adding the liquid passing through UM-10—no passing through UM-2 in the same amount of nitrogen as the yeast extract thereto.
6. Such one prepared by removing the yeast extract from the basic medium and adding the liquid passing through XM-100—no passing through UM-10 thereto in the same amount of nitrogen as the yeast extract.
7. Such one prepared by removing the yeast extract from the basic medium and adding the liquid no passing through XM-100 thereto in the same amount of nitrogen as the yeast extract.

100 ml of each of said prepared medium was put in a 500 ml Sakaguchi flask, and *Lentinus edodes* IFO 4902 (a species of japanese mushroom) was inoculated therein and incubated with shaking at 25° C. and 100 rpm (with 7 cm stroke).

After 7 days of culture, the propagated cells were collected by a filtration, and dried, and amount of cells in each medium was investigated as the dry matter.

The results are shown in the following Table, although the available component of the distillers solubles seems to have wide molecular weight distribution, it is obvious from the Table that the available component exists particularly in large quantities in the component passing through XM-100—no passing through UM-10 (molecular weight of about $10^4$–$10^5$).

TABLE

| Medium No. | Medium pH | Amount of cells (g/100ml) |
|---|---|---|
| 1 | 3.34 | 0.481 |
| 2 | 3.77 | 0.839 |
| 3 | 3.49 | 0.542 |
| 4 | 3.35 | 0.388 |
| 5 | 3.23 | 0.713 |
| 6 | 3.31 | 0.862 |
| 7 | 3.26 | 0.541 |

EXPERIMENTAL EXAMPLE 4

In the same manner as in Production example 11, pulverization treatment was carried out at various temperature in the entrance and exhaust zone, and after investigation of the state of resulting powder the following results were obtained:

| No. | Temperature (°C.) Entrance | Exhaust | State of the powder |
|---|---|---|---|
| 1 | 290–300 | 130–120 | No Good |
| 2 | 205–210 | 105–110 | Good |
| 3 | 150–160 | 95–85 | Good |

Using the powder thus obtained (No. 1, 2, 3), *Saccharomyces cererisiae* IFO 0203 was incubated with shaking for 40 hours at 28° C. and pH 5.5 by using the medium described in Production example 11, and also *Bacillus subtilis* IFO 3007 was incubated with shaking for 39 hours at 28° C. in the medium described in Production example 12. The results are shown in the following Table, and it is obvious from the Table that an activity decreases only a little by the treatment of pulverization.

TABLE

| | | B.subtilis | | S.cerevisiae | |
|---|---|---|---|---|---|
| No. | Component | $OD_{10}^{660}$ | Specific activity | $OD_{10}^{660}$ | Specific activity |
| 1 | Distillers solubles unconcentrated liquid | 0.490 | 1 | 0.625 | 1 |
| 2 | Powder 1 | 0.455 | 0.93 | 0.535 | 0.856 |
| 3 | Powder 2 | 0.483 | 0.99 | 0.535 | 0.865 |
| 4 | Powder 3 | 0.488 | 1 | 0.570 | 0.912 |

EXPERIMENTAL EXAMPLE 5

To the light fulvous transparent liquid obtained in Production example 1 ethanol was progressively added from 0% to 95% at ethanol final concentration, and after slow agitation, a precipitation occured at respective ethanol concentration. Each precipitation was isolated by filtration, then the amount of the solid matter and of sugars were determined. The results are shown in the following Table:

| | Ethanol final concentration (%) | | | | | |
|---|---|---|---|---|---|---|
| | 0–70 70% unsoluble section | 70–80 80% unsoluble section | 80–85 85% unsoluble section | 85–90 90% unsoluble section | 90–95 95% unsoluble section | 95–95% soluble section |
| Solid matter (%) | 10.8 | 8.4 | 2.5 | 2.5 | 3.5 | 72.4 |
| Sugars (%) | 9.6 | 3.0 | 0.9 | 1.4 | 1.5 | 81.4 |

Powder was respectively obtained by lyophile treatment of each unsoluble and soluble section obtained thus.

The powder above was added in such amount as corresponding to 25% of the defatted DS in 4 ml of the following medium:

Glucose—5 g
$KH_2PO_4$—0.5 g
$MgSO_4.7H_2O$—0.2 g
Polypeptone—0.42 g
add water to 100 ml and resulting medium containing the powder was adjusted at pH 70.

*Bacillus subtilis* IFO 3007 was inoculated in each medium thus obtained and incubated at 30° C. After 40 hours of culture, the propagation of cells was investigated.

The results are shown in the following Table, and it is obvious from the Table that a high activity exists in the 80% unsoluble section.

| | Control No added | Ethanol final concentration | | | | | |
|---|---|---|---|---|---|---|---|
| | | 0–70 70% unsoluble section | 70–80 80% unsoluble section | 80–85 85% unsoluble section | 85–90 90% unsoluble section | 90–95 95% unsoluble section | more than 95% 95% soluble section |
| Specific activity | 1.0 | 1.11 | 3.89 | 1.00 | 1.05 | 1.01 | 1.34 |
| activity | 1.0 | 1.10 | 3.93 | 1.01 | 1.02 | 1.02 | 1.23 |

EXPERIMENTAL EXAMPLE 6

With respect to the light fulvous transparent liquid obtained in Production example 1, the reverse osmosis membrane separation was carried out by using the RO reverse osmosis membrane of AS-215, AS-230 and AS-290 made by Abcor Co.

The characteristic of each RO reverse osmosis membrane used in the Example was as follows:

| RO reverse osmosis membrane | Inhibition ratio of sucrose |
|---|---|
| AS-215 | 15 ± 5% |
| AS-230 | 30 ± 10% |
| AS-290 | 90 ± 5% |

Using a solution containing 10% of sucrose

Using these reverse osmosis membranes, the liquid obtained in Production example 1 was treated at operation pressure of 20-21 Kg/cm² and water temperature of 25°-27° C., then liquid passing through the membrane and liquid remaining were respectively obtained. Each remaining percentage is shown in the following was respectively investigated by dry cell weight (dcw)

The results of the culture test are shown in the following Table:

| Incubation period | B. subtilis | | | | S. cerevisiae | | | | A. oryzae | |
|---|---|---|---|---|---|---|---|---|---|---|
| | $OD_{10}^{660}$ | | Specific activity | | $OD_{10}^{660}$ | | Specific activity | | dew (mg/100ml) | Specific activity |
| | 24hr(×10) | 38hr(×20) | 24 hr | 38 hr | 24hr(×10) | 38hr(×20) | 24 hr | 38 hr | 4 days | 4 days |
| Control 0 | 0.212 0.250 | 0.136 0.147 | 1 | 1 | 0.307 0.265 | 0.180 0.178 | 1 | 1 | 380.2 | 1 |
| Medium No. 1 | 0.308 0.313 | 0.195 0.203 | 1.34 | 1.41 | 0.600 0.570 | 0.351 0.343 | 2.05 | 1.94 | 523.8 | 1.38 |
| 2 | 0.406 0.440 | 0.255 0.275 | 1.83 | 1.87 | 0.527 0.542 | 0.310 0.313 | 1.87 | 1.74 | 318.9 | 0.84 |
| 3 | 0.297 0.287 | 0.183 0.174 | 1.26 | 1.26 | 0.592 0.595 | 0.360 0.348 | 2.08 | 1.98 | 612.0 | 1.61 |
| 4 | 0.420 0.420 | 0.315 0.320 | 1.82 | 2.24 | 0.530 0.555 | 0.315 0.358 | 1.90 | 1.88 | 308.3 | 0.81 |
| 5 | 0.300 0.330 | 0.170 0.208 | 1.36 | 1.34 | 0.613 0.610 | 0.392 0.346 | 2.14 | 2.07 | 608.3 | 1.60 |
| 6 | 0.378 0.370 | 0.292 0.318 | 1.62 | 2.16 | 0.593 0.580 | 0.365 0.348 | 2.05 | 1.99 | 303.6 | 0.80 |
| 7 | 0.312 0.318 | 0.270 0.298 | 1.36 | 2.01 | 0.720 0.682 | 0.475 0.467 | 2.45 | 2.63 | 631.8 | 1.66 |

Table;

| Medium No. | Treated liquid | Passing or remaining percentage | Amount of nitrogen (mg/ml) |
|---|---|---|---|
| 1 | Liquid no passing through AS-215 | 6 | 0.39 |
| 2 | Liquid passing through AS-215 | 94 | 0.09 |
| 3 | Liquid no passing through AS-230 | 5 | 0.35 |
| 4 | Liquid passing through AS-230 | 95 | 0.14 |
| 5 | Liquid no passing through AS-290 | 10 | 0.38 |
| 6 | Liquid passing through AS-290 | 90 | 0.15 |
| 7 | Untreated liquid | — | 0.54 |

Culture test was carried out by using each liquid of medium number in the Table above described.

(Mode of Culture Test)

Used strain: *Bacillus subtilis* IFO 3007, *Saccharomyces cerevisiae* IFO 0203, *Aspergillus oryzae* ATCC 128

Basic medium:
Medium for *B. subtilis*: glucose 5.0%, polypeptone 0.5%, $KH_2PO_4$ 0.5%, $MgSO_4.7H_2O$ 0.2%, pH 7.0
Medium for *S. cerevisiae*: glucose 5.0%, $(NH_4)_2SO_4$ 0.5%, $KH_2PO_4$ 0.1%, $MgSO_4.7H_2O$ 0.05%, $CaCl_2.2H_2O$ 0.01%, NaCl 0.01%, vitamin solution, pH 5.5
Medium for *A. oryzae*: glucose 3.0%, $K_2HPO_4$ 0.1%, KCl 0.05%, $MgSO_4.7H_2O$ 0.05%, $FeSO_4.7H_2O$ 0.001%, $NaNO_3$ 0.07%, pH 5.5

Preparation of medium and culture condition: Both *B. subtilis* and *S. cerevisiae* were cultured in the medium so adjusted that the all amount of nitrogen become equal by substituting respectively medium sample of said medium No. 1-7 for nitrogen source of the basic medium in the quantity of 30% (V/V). After 24 and 38 hours of culture with shaking at 28° C., the growth was respectively investigated by measuring $OD_{10}^{660}$. With respect to *A. oryzae*, after 4 days culture under these conditions the growth was respectively investigated by dry cell weight (dcw)

PRODUCTION EXAMPLE 1

100 ml of the distillers solubles unconcentrated liquid was subjected to a centrifugal separating treatment for 10 minutes at 13,000 rpm by means of KR-200A type centrifugal separator (made by Kubota Seisakusho) as it was.

The obtained liquid part was light fulvous and turbid with fine oil droplets.

This liquid part was filtered by means of Whatman No. 32 filter paper (Toyo Filter Paper No. 5C) and thereby 94 ml of light fulvous transparent liquid was obtained. The content of nitrogen thereof was 0.7 mg/ml.

PRODUCTION EXAMPLE 2

100 ml of the distillers solubles unconcentrated liquid was added with 4 g of Celite (Trade name: Supercell) and mixed therewith sufficiently, and then the mixture was filtered by means of a suction filter (Nutsche), thereby obtaining 94 ml of light fulvous transparent liquid.

PRODUCTION EXAMPLE 3

100 ml of the distillers solubles unconcentrated liquid was subjected to a centrifugal separating treatment at 9,000 rpm for 8 minutes (80,000 g×minutes) by means of KR-200A type centrifugal separator (Kubota Seisakusho).

The obtained liquid part was light fulvous and turbid with fine oil droplets.

This liquid part was filtered by means of Whatman No. 32 filter paper, and thereby 94 ml of light fulvous transparent liquid was obtained.

The obtained light fulvous transparent liquid was treated by means of a molecular sieve in which membrane filters, XM-100 and UM-10, made by Amicon Co., were set, and thereby the liquid part which passed through XM-100 and did not pass through UM-10 and thus remained was collected thereby obtaining 9.4 ml of light yellow transparent liquid. Content of nitrogen thereof was 3.4 mg/ml.

PRODUCTION EXAMPLE 4

100 ml of the distillers solubles unconcentrated liquid was subjected to a centrifugal separating treatment at 9,000 rpm for 8 minutes (80,000 g×minutes) by means of KR-200A type centrifugal separator (Kubota Seisakusho).

The obtained liquid part was light fulvous and turbid with fine oil droplets.

This liquid part was filtered by means of Whatman No. 32 filter paper, and thereby 94 ml of light fulvous transparent liquid was obtained. 200 ml of the obtained light fulvous transparent liquid (total nitrogen content 0.74 mg/ml) was treated by means of a molecular sieve in which membrane filter of UM-05, made by Amicon Co., was set, and thereby the liquid part which passed through it was collected, yielding 160 ml (total nitrogen content 0.14 mg/ml) of light fulvous transparent liquid.

PRODUCTION EXAMPLE 5

1,000 ml of the distillers solubles unconcentrated liquid was added with 40 g of Celite (Trade name: Super-cell), and mixed therewith sufficiently, and then the mixture was filtered by means of a suction filter (Nutsche), yielding 940 ml of light fulvous transparent liquid.

200 ml (total nitrogen content 0.74 mg/ml) of the obtained light fulvous transparent liquid was treated by means of a molecular sieve in which a membrane filter of UM-05, made by Amicon Co., was set, and thereby the liquid part which passed through it, yielding 160 ml (total nitrogen content 0.15 mg/ml) of light fulvous transparent liquid.

PRODUCTION EXAMPLE 6

30 ml of the light fulvous transparent liquid obtained in Production example 1 was mixed with the mixture consisting of $K_2HPO_4$ 0.1 g, KCl 0.05 g, $MgSO_4.7H_2O$ 0.05 g, $FeSO_4.7H_2O$ 0.001 g, glucose 3 g and $NaNO_3$ 0.07 g, adding water to 100 ml, adjusting pH 5.5, and thus a medium for molds being prepared.

PRODUCTION EXAMPLE 7

30 ml of the light fulvous transparent liquid obtained in Production example 1 was mixed with the mixture consisting of $NH_4Cl$ 0.12 g, glucose 5 g, $K_2HPO_4$ 0.1 g, $MgSO_4.7H_2O$ 0.3 g, and a small amount of vitamins, adding water to 100 ml, adjusting pH 5.5, and thus a medium for yeasts being prepared.

PRODUCTION EXAMPLE 8

30 ml of the light fulvous transparent liquid obtained in Production example 2 was pulverized by lyophile as it was. Thus obtained powder was mixed with the mixture consisting of glucose 5 g, $(NH_4)_2SO_4$ 0.4 g, $KH_2PO_4$ 0.1 g, $CaCl_2.2H_2O$ 0.01 g, $MgSO_4.7H_2O$ 0.05 g, NaCl 0.01 g and a small amount of vitamins in the dry powder state, and thereby a medium for yeasts being obtained.

This medium is instantly used for culture of yeast by adding water to 100 ml and adjusting pH 5.5 on the spot.

PRODUCTION EXAMPLE 9

6 ml of the light fulvous transparent liquid obtained in Production example 4 was mixed with the mixture consisting of glucose 5 g, $KH_2PO_4$ 0.5 g, $MgSO_4.7H_2O$ 0.2 g and polypeptone 0.42 g, adding water to 100 ml, adjusting pH 7.0, and thus a medium for Bacillus subtilis.

PRODUCTION EXAMPLE 10

30 ml of the light fulvous transparent liquid obtained in Production example 1 was mixed with the mixture of polypeptone 1.06 g, glucose 2 g, Na-acetate.$3H_2O$ 0.7 g, $K_2HPO_4$ 0.04 g, $KH_2PO_4$ 0.04 g, $MgSO_4.7H_2O$ 0.025 g, NaCl 0.001 g, $MnSO_4$ 0.001 g, $FeSO_4.7H_2O$ 0.001 g, K-citrate 0.003 g and $CaCO_3$ 1 g, adding water to 100 ml, and thus a medium for lactic acid bacteria being prepared.

PRODUCTION EXAMPLE 11

The light fulvous transparent liquid was pulverized as it was by means of spray dryer at 150°–300° C. of entrance temperature and at 85°–130° C. of exhaust temperature.

A medium for yeast was prepared by adding such amount of the resulting powder that corresponds to that of obtained by 30 ml of light fulvous transparent liquid to the following composition:

Glucose—5 g
$(NH_4)_2SO_4$—0.5 g
$KH_2PO_4$—0.1 g
$MgSO_4.7H_2O$—0.05 g
$CaCl_2.2H_2O$—0.01 g
NaCl—0.01 g
Vitamins—small amount
Water—100 ml
(pH=5.5)

PRODUCTION EXAMPLE 12

A medium for bacteria was prepared by adding such amount of the powder obtained in Production example 11 as corresponds to that of obtained by 30 ml of light fulvous transparent liquid to the following composition:

Glucose—5 g
Polypeptone—0.5 g
$KH_2PO_4$—0.5 g
$MgSO_4.7H_2O$—0.2 g
Water—100 ml
(pH=7.0)

PRODUCTION EXAMPLE 13

50 ml of the light fulvous transparent liquid obtained in Production example 1 was added with about 117 ml of ethanol, and the mixture was slowly agitated, thus formed precipitate was removed by filtration. The filtrate was further added with about 83 ml of ethanol, after slow agitation of the mixture, formed precipitate was isolated by filtration and air-dried.

PRODUCTION EXAMPLE 14

100 ml of the light fulvous transparent liquid obtained in Production example 1 was treated by means of RO reverse osmosis membrane "AS-230 (made by Abcor Co.)" at operation pressure of 20–21 Kg/cm² and water temperature of 25°–27° C., and thereby yielding 95 ml of the passing liquid.

The following examples illustrate culturing examples using the fermentation medium according to this invention. In these culturing examples, the light fulvous transparent liquid obtained in Production example 1 was referred as "defatted DS", that liquid obtained in Production example 3 was referred as "DS $10^4$–$10^5$", weight of the dry cells obtained by culturing were represented by "dcw (g)", and when the cells in culture fluids were measured by means of absorption at 660 nm, the amount of cells was represented by "absorbance".

CULTURING EXAMPLE 1

As the strain, *Aspergillus oryzae* ATCC 128 was used.
Glucose—3 g
$K_2HPO_4$—0.1 g
KCl—0.05 g
$MgSO_4.7H_2O$—0.05 g
$FeSO_4.7H_2O$—0.001 g
$NaNO_3$—Variation
Casamino acid—Change
Defatted DS—Change
DS $10^4$-$10^5$—Change
pH=5.5

The above compositions were become 100 ml by water.

An inoculation of the spore suspension of said strain was made to each of four new 500 ml-Sakaguchi flasks containing the medium of No. 1–4 prepared as following Table by using the basic medium above described. And a shaking culture was carried on for 4 days at 30° C.

| Medium No. | $NaNO_3$ | Casamino acid | Defatted DS | DS $10^4$-$10^5$ | Total-N |
|---|---|---|---|---|---|
| 1 | 0.2g | | | | 32.9mg |
| 2 | | 0.44g | | | 32.9 |
| 3 | 0.07 | | 30ml | | 32.9 |
| 4 | 0.14 | | | 6ml | 32.9 |

(in 100ml of medium)

The cells were filter separated from the obtained culture broth, and the weight of cells (dry matters), pH of the filtrate and residual sugar were measured.

The condition of drying the cells was at 110° C. and for 2 hours, and the quantitative determination of sugar was carried out by modified Somogyi's method.

The results were as follows:

TABLE

| Medium No. | N source g/100ml | dcw (g) | pH | Residual sugar(%) | Specific activity |
|---|---|---|---|---|---|
| 1 | $NaNO_3$ 0.2 | 0.400 | 4.2 | 0.45 | 1 |
| | | 0.416 | 4.5 | 0.51 | |
| 2 | Casamino acid 0.44 | 0.474 | 3.9 | 0.37 | 1.05 |
| | | 0.431 | 3.8 | 0.44 | 0.95 |
| 3 | $NaNO_3$ 0.07 | 0.769 | 3.7 | 0.24 | 1.70 |
| | Defatted DS 30ml | 0.745 | 3.7 | 0.17 | 1.65 |
| 4 | $NaNO_3$ 0.14 | 0.662 | 4.8 | 0.03 | 1.46 |
| | DS $10^4$-$10^5$ 6ml | 0.636 | 4.3 | 0.03 | 1.40 |

CULTURING EXAMPLE 2

As the strain, *Rhizopus delemar* IFO 4697 was used. A composition of the basic medium was as follows.
Glucose—3 g
$K_2HPO_4$—0.1 g
KCl—0.05 g
$MgSO_4.7H_2O$—0.05 g
$FeSO_4.7H_2O$—0.001 g
Polypeptone—Variation
Casamino acid—Change
Defatted DS—Change
DS $10^4$-$10^5$—Change
Adjust pH 5.5 and add water to 100 ml Said strain was incubated by using each medium of No. 1–4 prepared as following Table as described in Culturing example 1, except that it was incubated for 5 days.

| Medium No. | poly-peptone | Casamino acid | Defatted DS | DS $10^4$-$10^5$ | Total-N |
|---|---|---|---|---|---|
| 1 | 0.25g | | | | 32.9mg |
| 2 | | 0.44g | | | " |
| 3 | 0.09 | | 30ml | | " |
| 4 | 0.17 | | | 6ml | " |

(in 100ml of medium)

After culture the measurments were performed according to the procedure of Culturing example 1. The results were as follows:

| Medium No. | N source (g/100ml) | dcw (g) | pH | Residual sugar(%) | Specific activity |
|---|---|---|---|---|---|
| 1 | Polypeptone 0.25 | 0.231 | 2.4 | — | 1 |
| | | 0.223 | 2.4 | — | |
| 2 | Casamino acid 0.44 | 0.313 | 2.5 | — | 1.38 |
| | | 0.314 | 2.5 | — | 1.38 |
| 3 | Polypeptone 0.09 | 0.292 | 2.9 | — | 1.29 |
| | defatted DS 30ml | 0.277 | 2.9 | — | 1.22 |
| 4 | Polypeptone 0.17 | 0.256 | 2.6 | — | 1.13 |
| | DS $10^4$-$10^5$ 6ml | 0.277 | 2.6 | — | 1.22 |

CULTURING EXAMPLE 3

As the strain, *Saccharomyces cerevisiae* IFO 0203 was used. With respect to the medium, the following composition was used as the basic medium:
Glucose—5 g
$K_2HPO_4$—0.1 g
$MgSO_4.7H_2O$—0.3 g
Vitamins—small amount
Water—100 ml
(pH=5.5)

the basic medium above was added with $NH_4Cl$, defatted DS and/or DS $10^4$-$10^5$ as described in the following Table, and thereby the medium of No. 1–3 being respectively prepared:

| Medium No. | $NH_4Cl$ | defatted DS | DS $10^4$-$10^5$ | Total-N |
|---|---|---|---|---|
| 1 | 0.2g | | | 53mg |
| 2 | 0.12 | 30ml | | " |
| 3 | 0.16 | | 6ml | " |

(in 100ml of medium)

By using the medium of No. 1 above mentioned, a preculture was carried out by shaking culture at 30° C. for one night. The strains after preculture were inoculated in medium size test tubes containing 5 ml of medium in such manner that they were finally diluted a thousand times, and incubated with shaking (180 rpm) at 30° C. for 30 hours.

The growth of cells was measured by measuring absorbance at 660 nm of the culture fluids thus obtained.
The results were shown in the following Table.

TABLE

| Medium No. | N Source | Absorbance | Specific activity |
|---|---|---|---|
| 1 | $NH_4Cl$ 0.2g | 3.20 | 1 |
| 2 | $NH_4Cl$ 0.12g, defatted DS 30ml | 8.40 | 2.63 |

TABLE-continued

| Medium No. | N Source | Absorbance | Specific activity |
|---|---|---|---|
| 3 | NH$_4$Cl 0.16g, DS $10^4$-$10^5$ 6ml | 4.44 | 1.39 |

CULTURING EXAMPLE 4

Culture and measurment were carried out by using same medium, culture conditions, measuring method etc. as those described in Culturing example 3, except that *Candida tropicalis* IFO 0006 was used as strain. The results were shown in the following Table:

TABLE

| Medium No. | N source (g/100ml) | Absorbance | Specific activity |
|---|---|---|---|
| 1 | NH$_4$Cl 0.2 | 6.4 | 1 |
|  |  | 6.3 |  |
| 2 | NH$_4$Cl 0.12 | 14.6 | 2.30 |
|  | defatted DS 30ml | 14.8 | 2.32 |
| 3 | NH$_4$Cl 0.16 | 8.56 | 1.34 |
|  | DS $10^4$-$10^5$ 6ml | 9.40 | 1.48 |

CULTURING EXAMPLE 5

As the strain, *Pichia membranaefaciens* IFO 0128 was used. With respect to the medium, the following composition being used as the basic medium:
Glucose—3 g
KH$_2$PO$_4$—0.1 g
CaCl$_2$.2H$_2$O—0.01 g
MgSO$_4$.7H$_2$O—0.05 g
NaCl—0.01 g
Vitamins—small amount
Water—100 ml
(pH=5.5)
the basic medium above was added with (NH$_4$)$_2$SO$_4$, defatted DS and/or DS $10^4$-$10^5$ as described in the following Table, and thereby the medium of No. 1-4 being respectively prepared:

| Medium No. | (NH$_4$)$_2$SO$_4$ | Casamino acid | defatted DS | DS $10^4$-$10^5$ | Total-N |
|---|---|---|---|---|---|
| 1 | 0.5g |  |  |  | 10.6mg |
| 2 |  | 1.4g |  |  | " |
| 3 | 0.4 |  | 30ml |  | " |
| 4 | 0.46 |  |  | 6ml | " |

(in 100ml of medium)

Culture was carried out as described in Culturing example 4, except that the temperature was maintained at 25° C. Measuring the culture fluids thus obtained, the results are shown in the following Table: (The measuring method is the same as described in Culturing example 3)

TABLE

| Medium No. | N source (g/100ml) | Absorbance | Specific activity |
|---|---|---|---|
| 1 | (NH$_4$)$_2$SO$_4$ 0.5 | 3.92 | 1 |
|  |  | 3.70 |  |
| 2 | Casamino 1.4 acid | 4.21 | 1.10 |
|  |  | 4.80 | 1.26 |
| 3 | (NH$_4$)$_2$SO$_4$ 0.4 | 7.04 | 1.85 |
|  | defatted DS 30ml | 6.80 | 1.78 |
| 4 | (NH$_4$)$_2$SO$_4$ 0.46 | 5.90 | 1.55 |
|  | DS $10^4$-$10^5$ 6ml | 5.90 | 1.55 |

CULTURING EXAMPLE 6

As the strain, *Lactobacillus casei* IFO 3425 was used. With respect to the medium, the following composition being used as the basic medium:
Glucose—2 g
Na-acetate.3H$_2$O—0.7 g
K$_2$HPO$_4$—0.04 g
KH$_2$PO$_4$—0.04 g
MgSO$_4$.7H$_2$O—0.025 g
NaCl—0.001 g
MnSO$_4$—0.001 g
FeSO$_4$.7H$_2$O—0.001 g
K-citrate—0.003 g
CaCO$_3$—1 g
Water—100 ml
the basic medium above was added with polypeptone, yeast extract, defatted DS and DS $10^4$-$10^5$ as described in the following Table, and thereby the medium of No. 1-7 being respectively prepared:

| Medium No. | polypeptone | yeast extract | defatted DS | DS$10^4$-$10^5$ | Total-N |
|---|---|---|---|---|---|
| 1 | 1.22g |  |  |  | 160.8mg |
| 2 | 1.05 | 0.2g |  |  | " |
| 3 | 1.06 |  | 30ml |  | " |
| 4 | 1.14 |  |  | 6ml | " |
| 5 | 0.8 | 0.5 |  |  | " |
| 6 | 0.8 |  | 80 |  | " |
| 7 | 1.02 |  |  | 16 | " |

(in 100ml of medium)

10 ml of each medium was respectively transferred in medium size test tube. A preculture was carried out at 30° C. for one night by using the same medium as that of No. 5, and the inoculum size was adjusted as a thousand times dilution was finally obtained.

A culture was accomplished by stationary manner at 30° C. for 48 hours.

The culture broth obtained was respectively added with 1 ml. of lactic acid to dissolve calcium carbonate, adequately diluted, and then the absorbance thereof at 660 nm was measured.

The obtained results are shown in the following Table:

TABLE

| Medium No. | N source (g/100ml) | Absorbance | Specific activity |
|---|---|---|---|
| 1 | polypeptone 1.22 | 0.88 | 1 |
|  |  | 0.85 |  |
| 2 | polypeptone 1.05 | 1.41 | 1.63 |
|  | yeast extract 0.2 | 1.35 | 1.56 |
| 3 | polypeptone 1.06 | 1.69 | 4.53 |
|  | defatted DS 30ml | 1.71 | 4.09 |
| 4 | polypeptone 1.14 | 1.91 | 2.87 |
|  | $10^4$-$10^5$ DS 6ml | 1.51 | 3.03 |
| 5 | polypeptone 0.8 | 1.53 | 3.73 |
|  | yeast extract 0.5 | 1.43 | 3.63 |
| 6 | polypeptone 0.8 | 2.13 | 5.64 |
|  | defatted DS 80ml | 1.98 | 5.34 |
| 7 | polypeptone 1.02 | 1.75 | 3.80 |
|  | $10^4$-$10^5$ DS 16ml | 1.88 | 3.93 |

CULTURING EXAMPLE 7

Culture and measurement were carried out by using same medium, culture conditions, measuring method etc. as those described in Culturing example 6, except that *Leuconostoc mesenteroides* IFO 3832 was used.

The obtained results are shown in the following Table:

TABLE

| Medium No. | N source (g/100ml) | Absorbance | Specific activity |
|---|---|---|---|
| 1 | polypeptone 1.22 | 0.58 | 1 |
| | | 0.65 | |
| 2 | polypeptone 1.05 | 1.69 | 6.39 |
| | yeast extract 0.2 | 1.70 | 5.60 |
| 3 | polypeptone 1.06 | 2.20 | 6.97 |
| | defatted DS 30ml | 1.95 | 6.79 |
| 4 | polypeptone 1.14 | 1.78 | 6.11 |
| | DS $10^4$–$10^5$ 6ml | 1.74 | 5.89 |
| 5 | polypeptone 0.8 | 1.55 | 6.63 |
| | yeast extract 0.5 | 1.77 | 6.45 |
| 6 | polypeptone 0.8 | 2.50 | 8.94 |
| | defatted DS 80ml | 2.25 | 8.37 |
| 7 | polypeptone 1.02 | 2.35 | 7.65 |
| | DS $10^4$–$10^5$ 16ml | 2.25 | 7.31 |

CULTURING EXAMPLE 8

As the strain, *Streptomyces griseus* IFO 13189 was used. The medium was prepared as described in Culturing example 1, except that pH was adjusted to 7.0.

A preculture was respectively carried out in a 500 ml-Sakaguchi flask containing 100 ml of each medium of No. 1–4 at 30° C. for 5 days by using Czapek-Dox medium. After inoculation of 5 ml of each preculture, a shaking culture was carried out at 30° C. for 5 days (stroke: 7 cm, 114 rpm)

Thus obtained culture broth was subjected to a centrifugal separating treatment at 10,000 rpm for 10 minutes, and that, precipitate part was dried at 110° C. for 2 hours to be measured the weight of dry cells, and on the other hand as to that liquid part, the value of pH and residual sugar was respectively measured. The quantitative determination of sugar was carried out by modified Somogyi's method.

The results are as follows:

TABLE

| Medium No. | N source (g/100ml) | dcw(g) | pH | Residual sugar(%) | Specific activity |
|---|---|---|---|---|---|
| 1 | NaNO$_3$ 0.2 | 0.120 | 7.8 | 1.76 | 1 |
| | | 0.124 | 7.8 | 1.54 | |
| 2 | Casamino acid 0.44 | 0.134 | 7.2 | 0.04 | 1.10 |
| | | 0.133 | 7.3 | 0.04 | 1.09 |
| 3 | NaNO$_3$ 0.07 | 0.174 | 7.5 | — | 1.43 |
| | defatted DS 30ml | 0.171 | 7.4 | — | 1.41 |
| 4 | NaNO$_3$ 0.14 | 0.186 | 7.6 | — | 1.53 |
| | DS $10^4$–$10^5$ 6ml | 0.186 | 7.7 | — | 1.53 |

CULTURING EXAMPLE 9

Culture and measurement were carried out by using same medium, culture conditions, measuring method etc. as those described in Culturing example 8, except that *Streptomyces aureofaciens* IFO 12594 was used. The obtained results are shown in the following Table:

TABLE

| Medium No. | N source (g/100ml) | dcw (g) | pH | Residual sugar(%) | Specific activity |
|---|---|---|---|---|---|
| 1 | NaNO$_3$ 0.2 | 0.601 | 2.2 | — | 1 |
| | | 0.648 | 1.9 | — | |
| 2 | Casamino acid 0.44 | 0.699 | 1.9 | — | 1.12 |
| | | 0.735 | 2.2 | — | 1.18 |
| 3 | NaNO$_3$ 0.07 | 0.825 | 2.1 | — | 1.32 |
| | defatted DS 30ml | 0.784 | 2.1 | — | 1.26 |
| 4 | NaNO$_3$ 0.14 | 0.777 | 2.0 | — | 1.24 |

TABLE-continued

| Medium No. | N source (g/100ml) | dcw (g) | pH | Residual sugar(%) | Specific activity |
|---|---|---|---|---|---|
| | DS $10^4$–$10^5$ 6ml | 0.758 | 2.0 | — | 1.21 |

CULTURING EXAMPLE 10

Using the low molecular available component (liquid passing through UM-05) of distillers solubles obtained in Production example 4 and using such five strains as:
 a. *Saccharomyces cerevisiae* K7 IFO 0203
 b. *Candida tropicalis* IFO 0006
 c. *Bacillus subtilis* IFO 3007
 d. *Pichia membranaefaciens* IFO 0128
 e. *Leuconostoc mesenteroides* IFO 3832
each strain was respectively incubated in each medium. Distillers solubles unconcentrated liquid and each basic medium were used as control, and in case of culture an amount of nitrogen was so adjusted that it always becomes same.

With respect to the yeasts, the following composition was used as a basic medium:
 Glucose—5%
 (NH$_4$)$_2$SO$_4$—0.5%
 KH$_2$PO$_4$—0.1%
 MgSO$_4$.7H$_2$O—0.05%
 CaCl$_2$.2H$_2$O—0.01%
 NaCl—0.01%
 Vitamins—small amount
 (pH=5.5)

With respect to the culture of yeast, *Pichia membranaefaciens* was incubated with shaking at 25° C. for 40 hours and the other yeasts were incubated with shaking at 28° C. for 36 hours.

With respect to the bacteria, the following composition was used as a basic medium:
 Glucose—5%
 Polypeptone—0.5%
 KH$_2$PO$_4$—0.5%
 MgSO$_4$.7H$_2$O—0.2%
 (pH=7.0)

The following composition was used as a basic medium for *Leuconostoc mesenteroides*:
 Glucose—2.0%
 Yeast extract—0.5%
 KH$_2$PO$_4$—0.04%
 MgSO$_4$.7H$_2$O—0.025%
 MnSO$_4$—0.001%
 FeSO$_4$.7H$_2$O—0.001%
 CaCO$_3$—1.0%
 Polypeptone—0.8%
 Sodium acetate—0.5%
 K$_2$HPO$_4$—0.04%
 NaCl—0.001%
 FeSO$_4$.7H$_2$O—0.001%
 Pottassium citrate—0.003%
 pH 6.5

The bacteria were incubated with or without shaking at 28° C. for 39 hours.

Culturing method was as follows: The each basic medium above was added with the filtrate containing the low molecular available component of distillers solubles in various amount as described in the following Table, removing the nitrogen source from the basic medium in such amount as corresponding to the nitrogen content of the filtrate which was added to the basic medium (in case of *Leuconostoc mesenteroides*, yeast extract being removed as the nitrogen source), and thereby the medium always containing same amount of nitrogen was respectively prepared. For comparison, the two media were further prepared, one being that of added, in various amount, with the transparent defatted and unconcentrated liquid of the distillers solubles as it is, and the other being that of using only the basic medium as nitrogen source without adding anything. On these media each microorganism of from a to e was incubated, and after the culture fluids obtained being diluted ten times by volume, the quantities of cells propagated in each of media above mentioned were comparatively determined by turbidity.

The results obtained are given in Table below, and it is obvious from the Table that the low molecular available component of distillers solubles is an excellent factor for propagation of each microorganism:

| Adding ratio of the defatted DS (%) | Medium (1) $OD_{10}^{660}(\times 10)$ | Medium (1) Final pH | Medium (2) $OD_{10}^{660}(\times 10)$ | Medium (2) Final pH |
|---|---|---|---|---|
| 0 | 0.317 | 3.56 | 0.296 | 4.23 |
| 15 | 0.368 | 3.98 | 0.371 | 5.27 |
| 30 | 0.416 | 4.44 | 0.418 | 5.58 |
| 45 | 0.430 | 5.14 | 0.423 | 5.60 |
| 60 | 0.390 | 5.59 | 0.368 | 5.49 |

Concentration of N in the defatted DS: 0.53 mg/ml

CULTURING EXAMPLE 12

Using the defatted DS and simultaneously the sulfite waste liquor (SWL), the yeast was incubated.

1. Used strain: *Candida utilis* IFO 0619
2. Basic medium:

TABLE

| Defatted, unconcentrated liquid of distillers solubles | low molecular available component (liquid passing through UM-05) | S. cerevisiae $OD_{10}^{660}$ | S. cerevisiae specific activity | C. tropicalis $OD_{10}^{660}$ | C. tropicalis specific activity | B. subtilis $OD_{10}^{660}$ | B. subtilis specific activity | Pichia membranaefaciens $OD_{10}^{660}$ | Pichia membranaefaciens specific activity | Leuconostoc mesenteroides $OD_{10}^{660}$ | Leuconostoc mesenteroides specific activity |
|---|---|---|---|---|---|---|---|---|---|---|---|
| 1 | | 0.84 | | 1.15 | | 0.38 | | 0.230 | | 0.428 | |
| | | | 1.00 | | 1.00 | | 1.00 | | 1.00 | | 1.00 |
| | | 0.92 | | 1.26 | | 0.40 | | 0.260 | | 0.420 | |
| | | 1.82 | | 1.64 | | 1.37 | | 0.464 | | 0.442 | |
| 2 | 30 ml/100 ml (N=21.0 mg) | | 2.06 | | 1.37 | | 3.55 | | 1.84 | | 1.04 |
| | | 1.81 | | 1.66 | | 1.40 | | 0.440 | | 0.440 | |
| | | 1.96 | | 1.87 | | 1.31 | | 0.420 | | 0.460 | |
| 3 | 50 ml/100 ml (N=35.0 mg) | | 2.23 | | 1.47 | | 3.35 | | 1.78 | | 1.10 |
| | | 1.97 | | 1.68 | | 1.30 | | 0.450 | | 0.472 | |
| | | 2.09 | | 1.93 | | 1.13 | | 0.503 | | 0.503 | |
| 4 | 70 ml/100 mg (N=49.0 mg) | | 2.35 | | 1.62 | | 2.85 | | 1.99 | | 1.17 |
| | | 2.05 | | 1.98 | | 1.09 | | 0.470 | | 0.488 | |
| | | 1.34 | | 1.27 | | 1.41 | | 0.325 | | 0.327 | |
| 5 | 30 ml/100 ml (N=4.1 mg) | | 1.51 | | 1.02 | | 3.65 | | 1.30 | | 0.79 |
| | | 1.31 | | 1.18 | | 1.44 | | 0.310 | | 0.340 | |
| | | 1.44 | | 1.40 | | 1.39 | | 0.365 | | 0.398 | |
| 6 | 50 ml/100 ml (N=6.9 mg) | | 1.63 | | 1.16 | | 3.69 | | 1.50 | | 0.95 |
| | | 1.42 | | 1.39 | | 1.49 | | 0.372 | | 0.407 | |
| | | 1.56 | | 1.52 | | 1.40 | | 0.395 | | 0.458 | |
| 7 | 70 ml/100 ml (N=9.6 mg) | | 1.78 | | 1.23 | | 3.63 | | 1.58 | | 1.05 |
| | | 1.58 | | 1.45 | | 1.43 | | 0.378 | | 0.433 | |

Note; $OD_{10}^{660}$: measured value of the culture liquids diluted 10 times by volume

CULTURING EXAMPLE 11

Using the defatted DS the bakers yeast was cultured.

Mode of Incubation

The N-sources of the following media (1) and (2) were replaced with the defatted DS such that total content of nitrogen become equal with each other.

Culture medium (1): for preculture

As total sugar in molasses 1%, $(NH_4)_2SO_4$ 0.16%, $KH_2PO_4$ 0.014%, $MgSO_4.7H_2O$ 0.009%, K-citrate 0.05%, citric acid 0.01%, pH 5.6 (T.N=34 mg/100 ml)

Culture medium (2): for main culture

Add 4.52 ml of the liquid containing 0.655% of $(NH_4)_2SO_4$ and 1.22% of $(NH_2)_2CO$ to 100 ml of the liquid containing 1% of total sugar in molasses and 0.014% of $KH_2PO_4$ and adjust pH 5.6 (T.N=32 mg/100 ml).

The results are given in the Table below and this shows that the yeast was best propagated in case of adding the defatted DS in an amount of 45%:

$(NH_4)_2HPO_4$—0.089 g
$(NH_4)_2SO_4$—0.307 g
KCl—0.048 g
$MgSO_4.7H_2O$—0.078 g
SWL (total sugar 3.0%)—80 ml Add tap water to 100 ml and adjust pH 5.5.

The five times concentrated liquid of the defatted DS was respectively added to the basic medium in an amount of 20, 30, 50 and 70% expressed as the ratio of the unconcentrated liquid of the defatted DS, and at the same time the amount of ammonium sulfate was respectively reduced according to the amount of the defatted DS added thereto, and then each medium containing same amount of nitrogen was respectively prepared. The yeast was transferred to a 500 ml Sakaguchi flask containing 100 ml of each medium above. The flask was incubated with shaking at 30° C. for 30–40 hours.

The results are shown in the following Table:

| Amount of the defatted DS added thereto (%) | Number of cells × $10^{cells \times 10^9}$/ml After 22 hrs of culture | Number of cells × $10^{cells \times 10^9}$/ml After 40 hrs of culture | Residual sugar (%) |
|---|---|---|---|
| 1 | — | 0.47 | 0.74 | 0.86 |
| 2 | 20 | 0.72 | 1.30 | 0.46 |

-continued

| | Amount of the defatted DS added thereto (%) | Number of cells × $10^{cells×10^9}$/ml | | Residual sugar (%) |
|---|---|---|---|---|
| | | After 22 hrs of culture | After 40 hrs of culture | |
| 3 | 30 | 0.61 | 1.40 | 0.49 |
| 4 | 50 | 0.61 | 1.40 | 0.48 |
| 5 | 70 | 0.52 | 1.10 | 0.47 |

CULTURING EXAMPLE 13

Using the defatted DS, a n-paraffin assimilable yeast was incubated.
1. Used strain: *Candida lipolytica*
2. Basic medium: n-paraffin 5%, $NH_4Cl$ 0.5%, $KH_2PO_4$ 0.02%, $MgSO_4\cdot7H_2O$ 0.02%, $FeSO_4\cdot7H_2O$ 10 mg/l, $MnSO_4\cdot4H_2O$ 2 mg/l, $ZnSO_4\cdot7H_2O$ 2 mg/l, $CaCO_3$ 1%, yeast extract 0.1%.
3. Culture: The yeast extract was removed from the basic medium above, and an amount of nitrogen was replaced in certain ratio with the original liquid of the defatted DS. The medium thus obtained was used for culture. (T.N = 130 mg/100 ml)
4. Culturing conditions: Shaking culture (150 rpm) at 30° C. for 60 hours. Using a 500 ml Sakaguchi flask containing 30 ml of the medium. Inoculum size $10^5$/ml.

The results of culture are shown in the following Table, and it shows that the defatted DS replaces 0.1% of the yeast extract or it is much more effective in propagation of the yeast.

| Culture | Amount of the defatted DS added thereto (%) | Amount of cells $OD_{10}^{660}$ (×100) |
|---|---|---|
| 1 | 20 | 0.31 |
| 2 | 30 | 0.32 |
| 3 | 45 | 0.34 |
| 4 | 60 | 0.36 |
| 5 | 75 | 0.38 |
| 6 | 90 | 0.38 |
| Control | yeast extract 0.1% added | 0.32 |

CULTURING EXAMPLE 14

The defatted DS was concentrated to ⅓ volume under reduced pressure. To 50 ml of the concentrated liquid thus obtained, changing pH conditions, 50 ml of organic solvent was added, then 50% unsoluble fraction was isolated. To the residual liquid part 25 ml of organic solvent was further added, then 60% unsoluble fraction was isolated. To the residual liquid part 42 ml of organic solvent was added, then 70% unsoluble fraction was isolated, and similarly adding 83 ml of organic solvent to the liquid part then 80% unsoluble fraction was isolated, and further adding 250 ml of organic solvent to the liquid part the 90% unsoluble fraction was isolated. Thus remained liquid part was 90% soluble fraction.

The following strains were used:
Bacterium: *Bacillus subtilis* IFO 3007
Yeast: *Saccharomyces cerevisiae* IFO 0203
Mold: *Penicillium chrysogenum* IFO 4826
Antinomyces: *Streptomyces griseus* (Ray Fungus) IFO 13189

The basic medium and culture conditions were as follows:

| | Basic Medium | Culture Conditions |
|---|---|---|
| Bacterium | Glucose 5%<br>Polypeptone 0.5%<br>$KH_2PO_4$ 0.5%<br>$MgSO_4\cdot7H_2O$ 0.2%<br>(pH 7.0) | Inoculate a preculture (carried out at 30° C. for one night by using the basic medium) in such inoculum size that a thousand times dilution is finally obtained, and incubate with shaking at 30° C. for 24 hrs. |
| Yeast | Glucose 5%<br>$NH_4Cl$ 0.2%<br>$K_2HPO_4$ 0.1%<br>$MgSO_4\cdot7H_2O$ 0.3%<br>(pH 5.5) | Inoculate a preculture (carried out at 30° C. for one night by using the basic medium) in such inoculation size that a thousand times dilution is finally obtained, and incubate with shaking at 30° C. for 24 hrs. |
| Mold | Glucose 3%<br>$NaNO_3$ 0.2%<br>KCl 0.05%<br>$MgSO_4\cdot7H_2O$ 0.05%<br>$FeSO_4\cdot7H_2O$ 0.001%<br>(pH 5.5) | Inoculate a spore suspension of the used strain, and incubate with shaking at 30° C. for 4 days |
| Antinomyces | Glucose 3%<br>$NaNO_3$ 0.2%<br>KCl 0.05%<br>$MgSO_4\cdot7H_2O$ 0.05%<br>$FeSO_4\cdot7H_2O$ 0.001%<br>(pH 7.0) | Inoculate respective 5 ml of a preculture carried out for 5 days by using the basic medium, and incubate with shaking for 5 days. |

By using such one prepared by adding the defatted DS to the basic medium above mentioned in an amount of 30%, such one prepared by adding the fraction by organic solvent to the basic medium above mentioned in such amount of that corresponding to 30% of the defatted DS, and by using the basic medium as a control, an activity was expressed as specific activity. Each specific activity was respectively symbolized as follows:

| Specific activity | Less than 1.0 | 1.0–1.2 | 1.2–1.5 | 1.5–2.0 | 2.0–2.5 | More than 2.5 |
|---|---|---|---|---|---|---|
| symbol | − | ± | + | + + | + + + | + + + + |

With respect to each strain above, under these conditions a culture test was carried out with changing the fraction conditions.

The results shown in the following Tables were obtained:

a. Fractionation conditions
   Organic solvent: Ethanol
   pH at fractionation: 3.8
   Temperature at fractionation: 25° C.

| Fractionated samples | Strains | | | |
|---|---|---|---|---|
| | B.subtilis | S. cerevisiae | P. chrysogenum A.oryzae | St.griseus |
| 0–50% | + + + | − | ± | ± | + |
| 50–60 | + + + | − | ± | ± | − |
| 60–70 | + + + | − | ± | − | − |
| 70–80 | + + + | − | − | − | − |
| 80–90 | − | − | − | − | − |
| more than 90 | − | + + + | ± | + | + + |
| Defatted DS | + + + | + + + | + | + | + + | b. Fractionation conditions
   Organic solvent: Ethanol
   pH at fractionation: 7.0
   Temperature at fractionation: 25° C.

| Fraction-<br>ated samples | Strains | | | | |
|---|---|---|---|---|---|
| | B.subtilis | S. cer-<br>evisiae | A.oryzae | P.chryso-<br>genum | St.griseus |
| Precipitate occurred by pH adjusting and cooling | ++++ | − | ± | − | − |
| 0–50% | ++++ | − | ± | ± | + |
| 50–60 | − | − | − | − | − |
| 60–70 | − | − | − | − | − |
| 70–80 | − | − | − | − | − |
| 80–90 | − | − | − | − | − |
| more than 90 | − | +++ | ± | + | ++ |
| Defatted DS | ++++ | +++ | + | + | ++ | c. Fractionation conditions
   Organic solvent: Ethanol
   pH at fractionation: 3.8
   Temperature at fractionation: 5° C.

| Fraction-<br>ated samples | Strains | | | | |
|---|---|---|---|---|---|
| | B.subtilis | S. cer-<br>evisae | A.cryzae | p.chryso-<br>genum | St.ariseus |
| Precipitate occurred by pH adjusting and cooling | ++++ | − | ± | − | − |
| 0–50% | + | − | ± | ± | + |
| 50–60 | − | − | − | − | − |
| 60–70 | − | − | − | − | − |
| 70–80 | − | − | − | − | − |
| 80–90 | − | − | − | − | − |
| more than 90 | − | +++ | ± | ± | ++ |
| Defatted DS | ++++ | +++ | + | + | ++ | d. Fractionation conditions
   Organic solvent- Ethanol
   pH at fractionation: 3.8
   Temperature at fractionation: 5° C.

| Fraction-<br>ated samples | Strains | | | | |
|---|---|---|---|---|---|
| | B. subtilis | S. cer-<br>evisae | A.oryzae | P.chryso-<br>genum | St.griseis |
| Precipitate occurred by pH adjusting and cooling | +++ | − | − | − | − |
| 0–50% | +++ | − | − | + | + |
| 50–60 | +++ | − | − | − | − |
| 60–70 | +++ | − | − | − | − |
| 70–80 | ++ | − | − | − | − |
| 80–90 | − | − | − | − | − |
| more than 90 | − | +++ | ++ | + | ++ |
| Defatted DS | +++ | +++ | ++ | + | ++ | e. Fractionation conditions
   Organic solvent: Methanol
   pH at fractionation: 3.8
   Temperature at fractionation: 25° C.

| Fraction-<br>ated samples | Strains | | | | |
|---|---|---|---|---|---|
| | B.subtilis | S.cer-<br>evisae | A.oryzae | P.chryso-<br>genum | St.griseus |
| 0–50% | ++++ | − | ± | ± | + |
| 50–60 | +++ | − | − | − | − |
| 60–70 | +++ | − | − | − | − |
| 70–80 | +++ | − | − | − | − |
| 80–90 | ++ | − | − | − | − |
| more than 90 | ++ | +++ | ± | + | ++ |
| Defatted DS | ++++ | +++ | + | + | ++ | f. Fractionation conditions
   Organic solvent: Acetone
   pH at fractionation: 3.8
   Temperature at fractionation: 2.5° C.

| Fraction-<br>ated samples | Strains | | | | |
|---|---|---|---|---|---|
| | B.subtilis | S. cer-<br>evisiae | A.cryzae | P. chryso-<br>genum | St.griseus |
| 0–70% | +++ | − | + | + | + |
| 70–80 | +++ | − | − | − | + |
| 80–90 | − | − | − | − | + |
| more than 90 | − | ++ | + | + | + |
| Defatted DS | +++ | +++ | + | + | ++ |

CULTURING EXAMPLE 15

The microorganisms used in this culturing example were isolated and identified from the rumen of cattle by the Second Bacteria Research Section, the National Institute of Animal Health, the Ministry of Agriculture and Forestry, and they are stocked therein. These organisms are not deposited anywhere, however, they are validly stocked in said Research Section with each strain number, and they may be available without restraint.

The name of used strains and its strain numbers in this Example were as follows:
   *Selenomonas sp.* 4-1-25
   *Selenomonas sp.* 4-3-28
   *Selenomonas sp.* P-3-7
   *Streptococcus bovis* 3-cattle-13
   *Streptococcus bovis* 9809
   *Bacteroides ruminicola* Br-19189
   *Bifidbacterium* 31
   *Bacteroides brevis* 7S-6
   *Bacteroides brevis* 7-2-2
   *Butyrivibrio fibrisolvens* 2-40
   *Butyrivibrio fibrisolvenn* 7S-29
   *Butyrivibrio fibrisolvens* 7-33
   *Butyrivibrio fibrisolvens* 7-19
   *Eubacterium sp.* 7S-27
   *Bacteroides oralis* 7-4
   *Ruminococcus flavefaciens* A17
   *Negasphela elsdenii* 4-3-32
   *Buthyrivibrio sp.* 7-7
   *Buthyrivibrio sp.* 7S-30
   *Buthyrivibrio alactoacidigens* 7S-11

The used media were as follows:
(1) Basic medium
   Sugar (Glucose or Maltose)—10 g
   Polypeptone—10 g
   Yeast extract—10 g
   Cysteine-HCl—0.5 g
   0.1% Resazulin solution—1 ml
   *Salts solution A—6 ml
   *Salts solution B—6 ml add water to 1 l and adjust pH 6.9
*Salts solution A
  0.6% $K_2HPO_4$
Salts solution B
  $KH_2PO_4$—0.6%
  NaCl—1.2%
  $(NH_4)_2SO_4$—1.2%
  $MgSO_4.7H_2O$—0.12%
  $CaCl_2.2H_2O$—0.12%

(2) Media for experimentation
  A. Control medium
    Use the basic medium above as it was
  B. Medium added with the available component of distillers solubles The transparent light fulvous liquid obtained in Production example 1 (hereinafter designated as "defatted DS") was added in such amount that the content of defatted DS in the resulting liquid medium was equal to 30%, and supplying polypeptone to the same level as the medium, thus the following medium was prepared:
  Sugar (Glucose or Maltose)—10 g
  Polypeptone—17.1 g
  Cysteine-HCl—0.5 g
  0.1% Resazulin solution—1 ml
  Salts solution A—6 ml
  Salts solution B—6 ml
  Defatted DS—300 ml
  Adjust pH 6.9 and add water to 1 l.

The mode of experimentation by using the strains and media above was as follows:

Mode of Experimentation (1) Preculture
Use such one culturing on a slant culture containing rumen extract at 37° C. for 2 days.

(2) Inoculation
0.6 ml of the salts solution being respectively added to the preculture slant, thus a cell suspension of strain was prepared. An inoculation was carried out by adding a drop of the suspension into each test tube by means of same pipette.

Such operation was always carried out under gas ($CO_2$) jet conditions in order to keep anaerobic conditions.

(3) Culturing
Stationary culture at 37° C.

(4) Measurement
The growth of cells were measured by measuring the OD 660 nm after both 24 hours and 48 hours of culture.
The results obtained from this experiment are as follows:

| (Results in the experiment) | | $OD_{10}^{660}$ | |
|---|---|---|---|
| Species . Strain number | Medium | 24hrs | 48hrs |
| Selenomonas sp. 4-1-25 | A | 0.688 | 0.648 |
|  | B | 0.745 | 0.675 |
| Selenomonas sp. 4-3-28 | A | 0.313 | 0.698 |
|  | A | 0.313 | 0.698 |
|  | B | 0.176 | 0.691 |
| Selenomonas sp. P-3-7 | A | 0.684 | 0.674 |
|  | B | 0.725 | 0.715 |
| Streptococcus bovis 3-cattle-13 | A | 0.414 | 0.669 |
|  | B | 0.333 | 0.708 |
| Streptococcus bovis 9809 | A | 0.485 | 0.545 |
|  | B | 0.440 | 0.540 |
| Bacteroides ruminicola Br-19189 | A | 0.011 | 0.059 |
|  | B | 0.056 | 0.371 |
| Bifidbacterium sp. 31 | A | 0.441 | 0.526 |

-continued

| (Results in the experiment) | | $OD_{10}^{660}$ | |
|---|---|---|---|
| Species . Strain number | Medium | 24hrs | 48hrs |
|  | B | 0.690 | 0.620 |
| Bacteroides brevis 7S-6 | A | 0.185 | 0.085 |
|  | B | 0.520 | 0.480 |
| Bacteroides brevis 7-2-2 | A | 0.010 | 0.015 |
|  | B | 0.145 | 0.235 |
| Butyrivibrio fibrisolvens 2-40 | A | 0.014 | 0.020 |
|  | B | 0.00 | 0.105 |
| Butyrivibrio fibrisolvens 7S-29 | A | 0.00 | 0.00 |
|  | B | 0.158 | 0.107 |
| Butyrivibrio fibrisolvens 7-33 | A | 0.017 | 0.009 |
|  | B | 0.063 | 0.088 |
| Butyrivibrio fibrisolvens 7-19 | A | 0.00 | 0.004 |
|  | B | 0.161 | 0.114 |
| Eubacterium sp. 7S-27 | A | 0.015 | 0.291 |
|  | B | 0.046 | 0.707 |
| Bacteroides oralis 7-4 | A | 0.078 | 0.495 |
|  | B 0.075 | 0.601 | |
| Ruminococcus flavefaciens A-17 | A | 0.025 | 0.397 |
|  | B | 0.001 | 0.522 |
| Necasphela elsdenii 4-3-32 | A | 0.011 | 0.009 |
|  | B | 0.030 | 0.555 |
| Butyrivibrio sp. 7-7 | A | 0.034 | 0.020 |
|  | B | 0.082 | 0.200 |
| Butyrivibrio sp. 7S-30 | A | 0.00 | 0.00 |
|  | B | 0.162 | 0.113 |

The following facts became clear from the results obtained by the experiments above described:

(1) The strains which grew only in the medium B (defatted DS added) were as follows:
  Negasphela elsdenii 4-3-32
  Butyrivibrio fibrisolvens 7S-29
  Butyrivibrio fibrisolvens 7-33
  Butyrivibrio fibrisolvens 2-40
  Butyrivibrio fibrisolvens 7-19
  Butyrivibrio sp. 7S-30
  Butyrivibrio alactoacidigens 7S-11
  Bacteroides brevis 7-2-2

(2) The strains which grew much more in the medium B (defatted DS added) than in the medium A (defatted DS no added) were as follows:
  Bacteroides ruminicola ATCC-19189
  Bacteroides brevis 7S-6
  Eubacterium sp. 7S-27
  Bifidbacterium thermophilum 31
  Ruminococcus flavefaciens A-17
  Bacteroides oralis 7-4

(3) The strains which grew well both in the medium A and in the medium B (there being not appreciable difference between those media) were as follows0
  Selenomonas sp. 4-1-25
  Selenomonas sp. 4-3-28
  Selenomonas sp. P-3-7
  Streptococcus bovis 3-cattle-13
  Streptococcus bovis 9809

The Feed examples according to the present invention are as follows:

FEED EXAMPLE 1

A basic composition used was as follows:
  Yellow corn—570 Kg
  Tallow—25 Kg
  Soybean cake—255 Kg
  Fish meal (crude protein content: 60%)—50 Kg
  Gluten meal—20 Kg
  Alfalfa meal—20 Kg
  Calcium phosphate—15 Kg Calcium carbonate—7.5 Kg
Sodium chloride—4.5 Kg
Magnesium sulfate—0.3 Kg
Zinc oxide—0.1 Kg
Methionine—0.3 Kg
Vitamins—5 Kg The composition above was added with 800 l of the transparent light fulvous liquid and all amount of the powder respectively obtained in Production examples 1 and 6, mixing them well, then a feed for broiler was prepared.

FEED EXAMPLE 2

A basic composition used was as follows:
Soybean cake (crude protein content: 44%)—250 Kg
Alfalfa meal—70 Kg
Molasses—70 Kg
Ground bones—25 Kg
Sodium chloride—8 Kg
Vitamin A (10,000 I.U./g)—0.8 Kg
Vitamin $D_2$(1,500 I.U./g)—0.3 Kg The composition above was added with 2,800 l of the transparent light fulvous liquid and all amount of the powder respectively obtained in Production examples 2 and 7, mixing them well, them a feed for beef cattle was prepared.

FEED EXAMPLE 3

A basic composition used was as follows:
Yellow corn—410 Kg
Milo—480 Kg
Soybean cake (crude protein content: 44%)—40 Kg
Fish solubles (crude protein content: 33%)—10 Kg
Calcium carbonate—7.5 Kg
Calcium phosphate—10 Kg
Sodium chloride—3 Kg
Minerals—2 Kg
Indian millet—480 Kg The composition above was added with 1,600 l of the transparent light fulvous liquid obtained in Production example 2, mixing them well, drying and then a feed for pig was prepared.

FEED EXAMPLE 4

A basic composition used was as follows:
Corn—440 Kg
Soybean cake (crude protein content: 44%)—75 Kg
Powdered meat—180 Kg
Powdered embryo—85 Kg
Tallow—50 Kg
Pressed wheat—25 Kg
Alfalfa meal—15 Kg
Grated cheese—15 Kg
Powdered fish—15 Kg
Powdered liver—7.5 Kg
Ground bones—10 Kg
Sodium chloride—10 Kg
Vitamin A (4,000 I.U./g)—1.5 Kg
Vitamin $D_2$(1,500 I.U./g)—1 Kg The composition above was added with 2,300 l of the transparent light fulvous liquid and all amount of the passing liquid respectively obtained in Production example 1 and 8, mixing them well, drying, and then a dog food was prepared.

FEED EXAMPLE 5

A basic composition used was as follows:
Wheat flour—50 Kg
White powdered fish—150 Kg
Oat—110 Kg
Powdered meat and Ground bones (crude protein content: 50%)—225 Kg
Soybean cake—50 Kg
Alfalfa meal—50 Kg
Cotton seed cake—50 Kg
Powdered embryo—50 Kg
Powdered liver—25 Kg
Skim milk powder—70 Kg
Sodium chloride—20 Kg The composition above was added with 5,000 l of the transparent light fulvous liquid obtained in Production example 2, mixing them well, granulating and then a bait for trout was prepared.

What is claimed is:

1. In a fermentation medium for the propagation of cells for use as food products, comprising fermentation medium ingredients selected from the group consisting of sugars, polypeptone, amino acid, ions of potassium and phosphate, and mixtures thereof, the improvement wherein said fermentation medium further comprises a growth factor of molecular weight of $10^3$–$10^5$ derived from distillers solubles by pretreatment with
(1) a centrifugal separation to a degree of above 50,000 (g×minute), or
(2) a filtration with addition of filter aid,
followed by collection of liquid containing molecular weight range of $10^3$–$10^5$ by subjecting the obtained clarified liquid to a molecular sieve treatment.

2. A fermentation medium according to claim 1, wherein said growth factor is dried, after said collection, by spray drying, lyophilization or air drying.

3. A fermentation medium according to claim 1, wherein said growth factor is obtained by said filtration.

4. A fermentation medium according to claim 1, wherein said growth factor is obtained by said centrifugal separation.

5. A fermentation medium according to claim 1, wherein said growth factor is obtained by centrifugal separation to a degree of at least 70,000 (g×minute).

* * * * *